United States Patent [19]
Schneider

[11] Patent Number: 5,888,195
[45] Date of Patent: Mar. 30, 1999

[54] LARYNGOSCOPE BLADE

[76] Inventor: Cary N. Schneider, 1609 Watch Hill Dr., Plano, Tex. 75093

[21] Appl. No.: 48,068

[22] Filed: Mar. 26, 1998

[51] Int. Cl.[6] .............................. A61B 1/267; A61B 1/06
[52] U.S. Cl. .......................... 600/199; 600/191; 600/194
[58] Field of Search .................................. 600/190, 199, 600/191, 210, 194, 197, 198

[56] References Cited

U.S. PATENT DOCUMENTS

| | | |
|---|---|---|
| 2,354,471 | 7/1944 | Macintosh . |
| 3,638,644 | 2/1972 | Reick . |
| 3,771,514 | 11/1973 | Huffman et al. . |
| 3,856,001 | 12/1974 | Phillips . |
| 4,556,052 | 12/1985 | Muller ...................................... 600/199 |
| 4,565,187 | 1/1986 | Soloway .................................. 600/199 |
| 4,573,451 | 3/1986 | Bauman . |
| 4,901,708 | 2/1990 | Lee ........................................ 600/199 |
| 5,003,962 | 4/1991 | Choi ....................................... 600/199 |
| 5,036,835 | 8/1991 | Filli . |
| 5,060,633 | 10/1991 | Gibson .................................... 600/199 |
| 5,065,738 | 11/1991 | Van Dam . |
| 5,095,888 | 3/1992 | Hawley ................................... 600/199 |
| 5,406,941 | 4/1995 | Roberts . |
| 5,603,688 | 2/1997 | Upsher . |
| 5,651,761 | 7/1997 | Upsher ................................... 600/194 |

FOREIGN PATENT DOCUMENTS

| | | |
|---|---|---|
| 522807 | 10/1953 | Bulgaria ................................. 600/191 |
| 0184588 | 6/1986 | European Pat. Off. . |
| 2102294 | 2/1983 | United Kingdom . |
| 2102679 | 2/1983 | United Kingdom . |
| 94/03101 | 2/1994 | WIPO . |
| 97/17885 | 5/1997 | WIPO . |

*Primary Examiner*—Paul J. Hirsch
*Attorney, Agent, or Firm*—Richard C. Litman

[57] ABSTRACT

An improved laryngoscope blade for use with a conventional laryngoscope handle and conventional means for illumination. The improvements to the blade include a small reverse curve at the tip of the blade to better visualize the depth of insertion of the blade, include a greater width of the portion of the blade proximal to the handle to provide improved means for controlling the tongue, and include a more gradual curvature of the blade to better conform to the shape of the airway opening when the patient is properly positioned for laryngoscopy. The blade may also include a vertical wall which may be thickened to serve as a bite block, and raised areas to define grooves on the surface of the blade for insertion of an endotracheal tube and/or a suction catheter.

7 Claims, 4 Drawing Sheets

LARYNGOSCOPE BLADE

BACKGROUND OF THE INVENTION

1. Field of the Invention

The present invention relates to laryngoscopes, and particularly to an improved blade for a laryngoscope.

2. Description of the Related Art

While a laryngoscope may be used to visually examine the larynx, its more important function is to aid in endotracheal intubation. The need for intubation may arise during a controlled situation, such as surgery, or in a crisis situation when the patient is unable to breathe adequately and requires a resuscitation bag or mechanical ventilation. During intubation, a flexible tube is inserted through the nasal or oral cavity, passed through the larynx, and into the trachea for the administration of gases. The larynx may be viewed as a chamber bounded superiorly by the epiglottis, inferiorly by the vocal cords which cover the opening to the trachea, anteriorly by the thyroid cartilage or Adam's apple, and posteriorly by a portion of the pharynx. The epiglottis is a lamella or leaf-like plate of cartilage which extends dorsally like a loose lid over the larynx, helping to protect the trachea by preventing food from entering the trachea during swallowing.

In order to intubate the patient, the intubator (either a physician or paramedic) must visualize the epiglottis and the vocal cords to watch the tube go past the vocal cords of the patient. The laryngoscope generally comprises a handle, a blade which is used to move the patient's tongue out of the way and to lift the epiglottis to expose the vocal cords, and a light source to illuminate the glottis and vocal cords.

The two most widely used blades in the current state of the art are known as the Miller blade and the Macintosh blade. The Miller blade is a substantially straight blade with a curved tip, the curve commencing approximate 2 inches from the end of the blade. The Macintosh blade is a blade which is curved for substantially its entire length (U.S. Pat. No. 2,354,471 issued Jul. 25, 1944). In use the Miller blade is inserted along the longitudinal axis of the larynx past the epiglottis to lift it enough to visualize the vocal cords and slip the tube through the cords into the trachea. The Macintosh blade is inserted on a combination of the axis of the oral cavity and the longitudinal axis of the larynx, the tip being placed in the vallecula, which are shallow depressions in the membranous folds and tissue between the epiglottis and the root of the tongue. By applying an upward pressure at the vallecula, the epiglottis is raised enough to visualize the vocal cords.

While intubation may be done with the existing blades, several shortcomings in the existing blades have prompted various efforts to improve the blades. Efforts to improve the curvature of the blade are shown in U.S. Pat. No. 5,003,962, issued Apr. 2, 1991 to Choi, and U.S. Pat. No. 5,406,941 issued Apr. 18, 1995 to Roberts. Choi describes a blade having three straight segments, the second segment at a 20 degree angle to the first, and the third at a 30 degree angle to the second. The Roberts patent describes a flat, flexible blade, having a cam attached to one side of the blade so the curvature may be adjusted by rotating the cam. U.S. Pat. No. 3,856,001 issued to O. C. Phillips Dec. 24, 1974 describes a Jackson or straight blade having a U-shaped cross-section and a tip similar to the Miller blade, curving about 2 inches from its end.

Efforts to improve the tip are shown in U.S. Pat. No. 4,573,451, issued Mar. 4, 1986 to Bauman, and U.S. Pat. No. 5,603,688 issued Feb. 18, 1997 to Upsher. The Bauman patent describes a blade made of plastic or metal, thinned or hinged at the tip, with a push rod and a ratchet to change the angle of the tip. Upsher's patent shows a blade having a hollow tube in the blade for insertion of the endotracheal tube, with an extension of one side of the tip to prevent the natural curve of the endotracheal tube from causing the end of the endotracheal tube to leave the field of vision after exiting the hollow tube in the blade.

Efforts to improve the illumination of the larynx and vocal cords are shown in U.S. Pat. No. 3,638,644 issued Feb. 1, 1972 to Reick, and U.S. Pat. No. 3,771,514 issued Nov. 13, 1973 to Huffman, et al. The Reick patent shows a light bulb in the handle with a plastic light conduit extending through the blade. The Huffman patent shows a one-piece handle and blade, the blade having a prism mounted thereon for reflecting and diffusing the light.

U.S. Pat. No. 5,036,835 issued Aug. 6, 1991 to Filli describes a blade which slides to adjust the length of the blade. U.S. Pat. No. 5,065,738 describes a sheath fitting over the blade to protect the patient's teeth, gums, oral mucosa and epiglottis from damage during insertion of the laryngoscope.

Various patents show a disposable blade, including European Patent 0184588 published Jun. 18, 1986, describing a disposable blade with a light source in the handle; International Patent 94/03101 published Feb. 17, 1994, describing a disposable blade with the light source in the blade; and International Patent 97/17885 published May 22, 1997, showing a disposable blade with a channel in the blade for the passage of fluids.

Construction techniques for incorporating a channel or path for a bulb and light cable or guide are shown in U.K. Patent 2,102,294 published Feb. 2, 1983, describing two L-shaped members put together in overlapping fashion to form a channel for the light and cable, and U.K. Patent 2,102,679 describing a blade made by placing a fiber optic bundle in an injection mold and forming a plastic blade by injecting the mold with plastic.

None of the above inventions and patents, taken either singularly or in combination, is seen to describe the instant invention as claimed. Thus an improved laryngoscope blade solving the aforementioned problems is desired.

The present invention exploits the principle used by health care providers to widen the airway in preparation of intubation. When the head is in the normal anatomic position, the airway is narrow. It is therefore recommended that the intubator align the laryngeal and pharyngeal axes; unlike the present invention, in this position neither the Miller blade nor the Macintosh blade present the optimum angle for viewing and intubating the patient. Although the Macintosh blade is curved, the curvature is greater than the curvature of the airway, hence it does not permit optimal visualization of the vocal cords because the intubator can't see around the curvature of the blade. Moreover, with both the Miller blade and the Macintosh blade, the intubator has difficulty visualizing the tip of the blade, again due to the shape of the blade and the shape of the airway. Consequently the intubator has difficulty determining when the tip is in proper position.

SUMMARY OF THE INVENTION

Accordingly, it is a principal object of the invention to provide an improved laryngoscope blade which produces better visualization of the larynx through adjusting the curvature of the blade.

The present invention is a laryngoscope blade which is generally curved throughout its length. However, the curvature is more gradual than the curvature of the conventional Macintosh blade.

The invention also provides the tip of the blade with a small reverse curve at the tip of the blade, in order to permit better visualization of the position of the end of the blade.

The laryngoscope blade of the present invention further includes a proximal part which is contoured to the width and shape of the mouth, having a width of up to 6 cm., in order to provide better control of the tongue during laryngoscopy. This configuration is unlike the part of a conventional laryngoscope blade proximal to its connection with the handle, which is used to move the tongue away from the airway and prevent the tongue from obstructing visualization of the larynx. Therefore, present laryngoscope blades have a maximum width of approximately 2 cm.

It is a further object of the invention to provide improved elements and arrangements thereof for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The present invention relates to a laryngoscope with an improved blade. A conventional laryngoscope typically comprises a handle, a blade, and a light source. The blade is usually pivotally mounted on the handle so that the blade is substantially parallel to the handle when not in use, and is substantially perpendicular to the handle to form an L-shape in use.

A variety of arrangements may be used to provide a light source. Power for the light source is usually provided by batteries in the handle. The light source itself may be in the handle with a conduit mounted on the blade, or the light source itself may be mounted on the blade. The connector used to mount the blade may vary depending on the nature of the light source.

Figure 1:
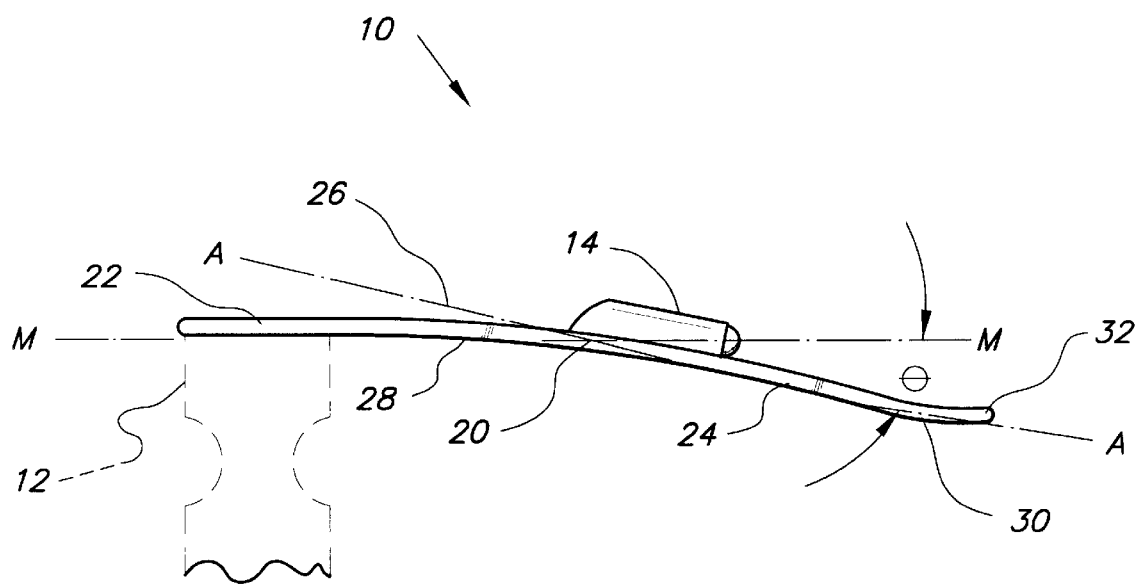
FIG. 1 is a right side view of the improved laryngoscope blade according to the present invention.
Figure 2:
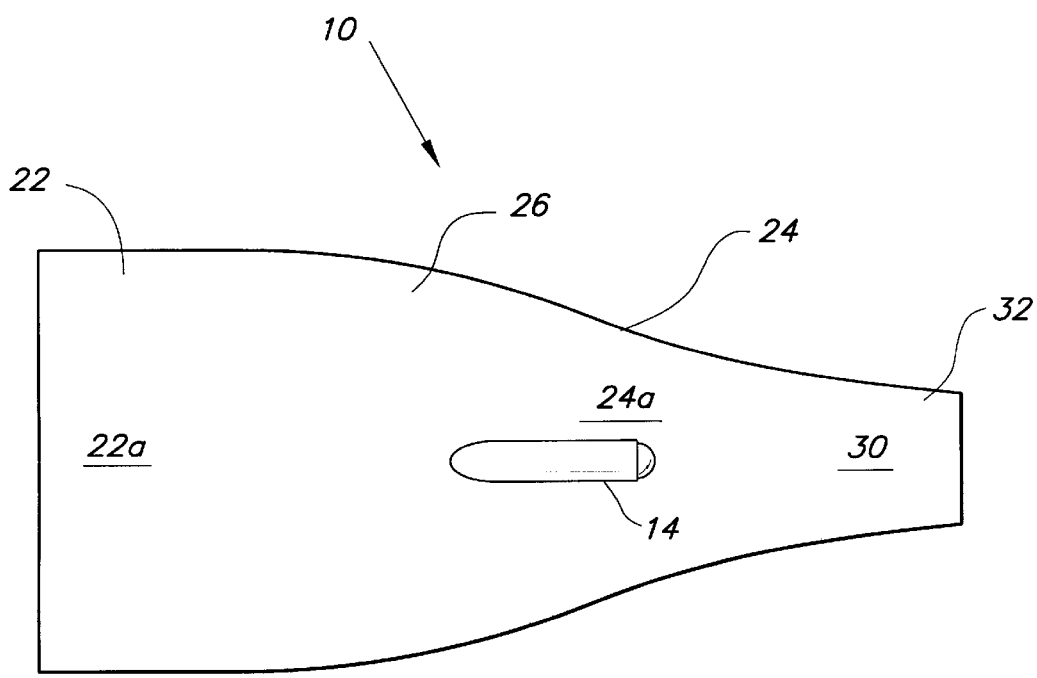
FIG. 2 is a top plan view of the improved laryngoscope blade according to the present invention.
Figure 3:
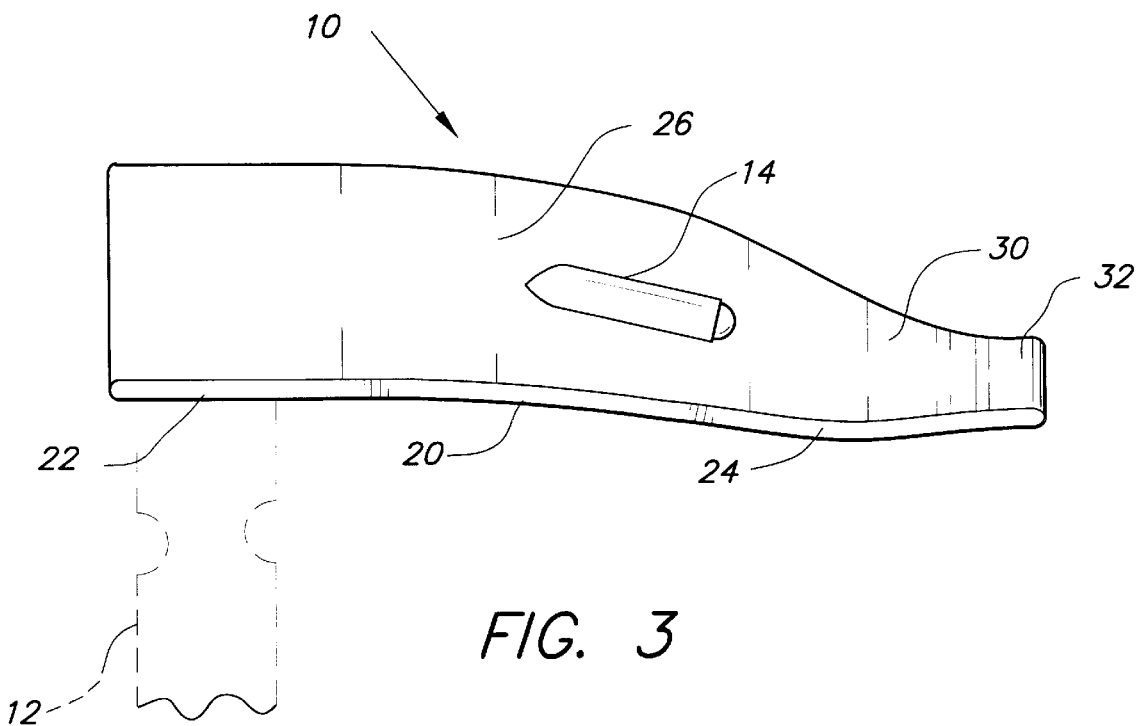
FIG. 3 is a top perspective view of the improved laryngoscope blade according to the present invention.
Figure 4:
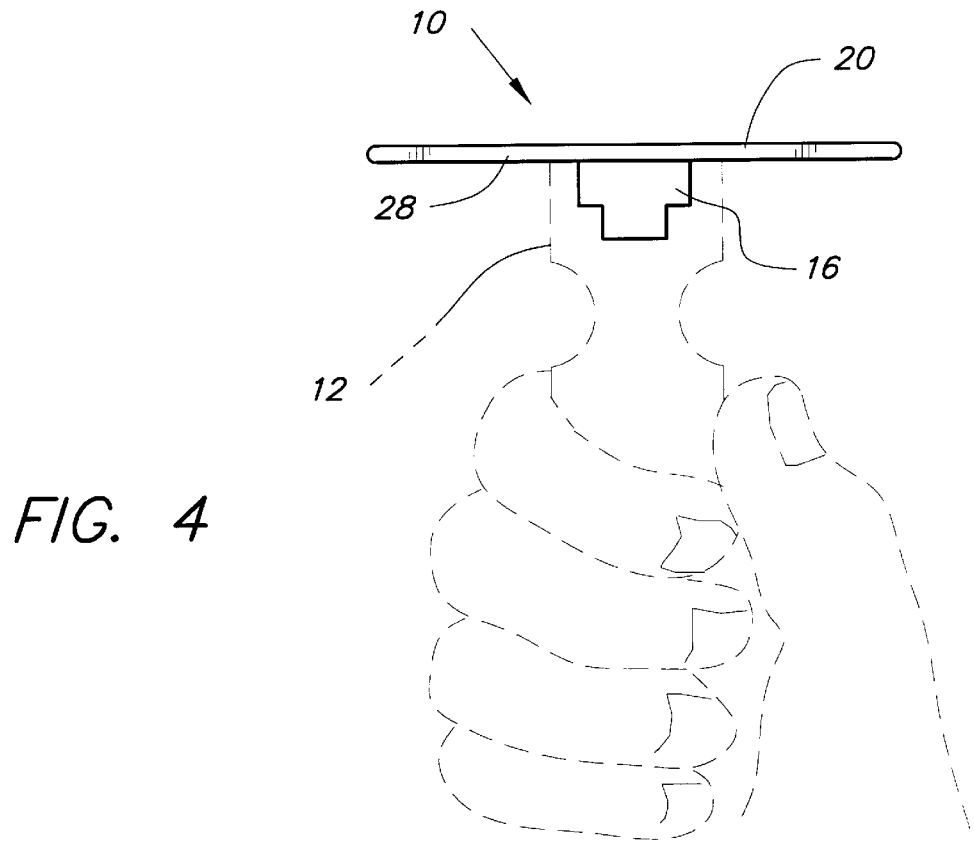
FIG. 4 is an end view of the improved laryngoscope blade according to the present invention.
Figure 5:
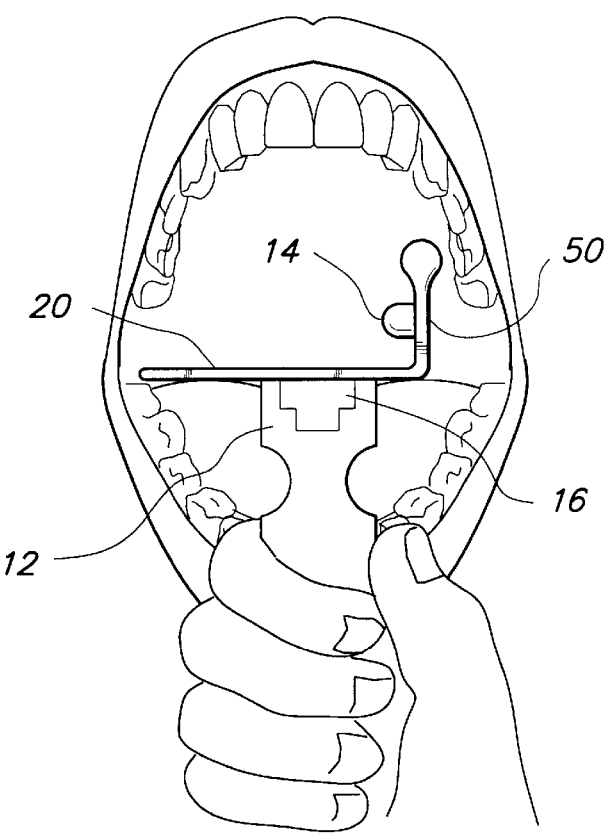
FIG. 5 is an environmental perspective view of an alternative embodiment of the invention showing a "bite block".

The improvement of the present invention does not relate to the handle, the light source, or the means connecting the blade to the handle. As shown more particularly in FIGS. 1 through 4, the present invention relates to the laryngoscope blade 10. The improved blade is designed to be used with a conventional handle 12 (shown in phantom in the drawings), means for illumination 14, and means 16 for connecting the blade 10 to the handle 12, all of which are well known in the prior art. Although the light source 14 is shown mounted on the top surface of the blade 10 in FIGS. 1 through 3, it will be appreciated that the light source 14 may be mounted alternatively on the edge of the blade 10, or in the handle 12 with a light-transmitting conduit towards the end of the blade 10, etc. The nature and location of the means for illumination 14 are not critical, provided that there are some means for illuminating the distal end of the blade 10 and an appropriate means 16 for connecting the blade 10 to the handle 12 adapted to the particular light source used.

The improved blade 10 has an arcuate body 20 having a proximal end 22 and a distal end 24, the body 20 being substantially flat, having a top surface 26 which is convex upwards as seen from a side view, and a bottom surface 28 concave downwards. The means 16 for connecting the blade 10 to the handle 12 is connected to the bottom surface 28 of the proximal end 22 of the body 20. The blade 10 has a tip 30 at the distal end 24 of the body 20, the tip 30 having a point of inflection as seen from a side view, most clearly seen in FIG. 1, and a short tip extension 32 being concave upwards. The tip extension 32 provides the physician or other person performing the intubation with a visual means for determining the depth to which the blade 10 has been inserted into the patient's throat, and can be rested on the top of the epiglottis, both features being an improvement on prior laryngoscope blades.

The top surface 26 and the bottom surface 28 of the blade 10 have a proximal portion 22a towards the proximal end 22 of the body 20 having a width of between 2 cm and 6 cm in the preferred embodiment, the proximal portion 22a having a substantially oblong shape, so the that proximal portion 22a conforms to the width of an adult patient's mouth. The top surface 26 and the bottom surface 28 have a distal portion 24a towards the distal end 24 of the body 20. The width of the blade 10 tapers from the proximal portion 22a to a width not greater than approximately 2 cm at the distal end 24, so that the distal end 24 may be inserted in the patient's throat.

It is contemplated that the blade 10 will be made in various sizes, with perhaps the width of the proximal portion of the body 20 ranging between 2 cm and 6 cm in 0.5 cm increments, while the distal end 24 perhaps ranges in width from 0.5 cm to 2 cm for the adult patient. For children and infants, the widths may be proportionally shorter, e.g., 1 cm for children and 0.5 cm f or infants. In an alternative embodiment, the proximal end 22 of the blade 10 may have a width greater than 6 cm to accommodate patients with a very large oral cavity. The greater width of the improved blade 10 at its proximal end 22 provides the physician or other intubator an improved means for controlling the patient's tongue during the intubation procedure.

In order to derive full advantage from the improved tip 30 and tip extension 32 of the present invention, the curvature of the arcuate body 20 should fall within certain limits. The conventional Macintosh blade has a rather steep curvature in order to facilitate passage over the tongue and to avoid depression of the tongue which might otherwise cause restriction of the visible aperture of the larynx. However, the conventional Macintosh is curved too much. Occasionally the physician or intubator can't see around the curvature of the Macintosh blade to view the larynx.

The blade of the present invention has a gentler curvature. When intubating a patient, it is recommended that the patient be positioned to align an axis extending through the pharynx with an axis extending through the larynx, or in other words, the opening to the airway is widened by straightening the throat. When so positioned, the angle between the pharyngeal axis and the laryngeal axis is approximately 5° to 25°. The blade 10 of the present invention is designed to conform with this angle.

Viewing the blade 10 from the side, a median axis M extending longitudinally through the bottom surface of the proximal portion 22a of the arcuate body 20 intersects with a median axis A extending longitudinally through the distal portion 24a of the body 20 to define an angle θ. In the blade 10 of the present invention, this angle θ is between 5° and 25°, preferably approximately 15°. The more gradual curvature of the blade 10 of the present invention facilitates viewing the tip extension 32 when the blade 10 is inserted in the patient's throat.

Figure 6:
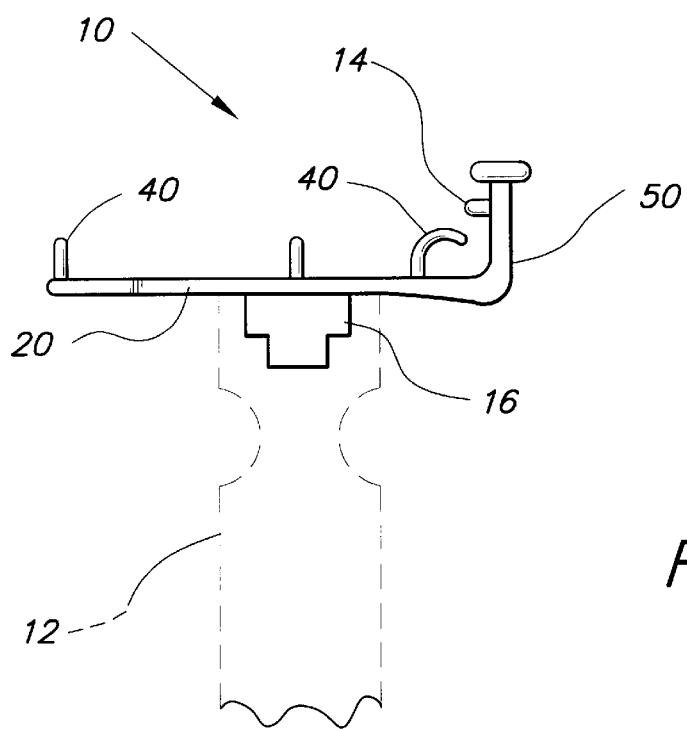
FIG. 6 is an end view of an alternative embodiment of the invention showing a "bite block" and raised areas on the surface of the blade defining grooves.
Figure 7:
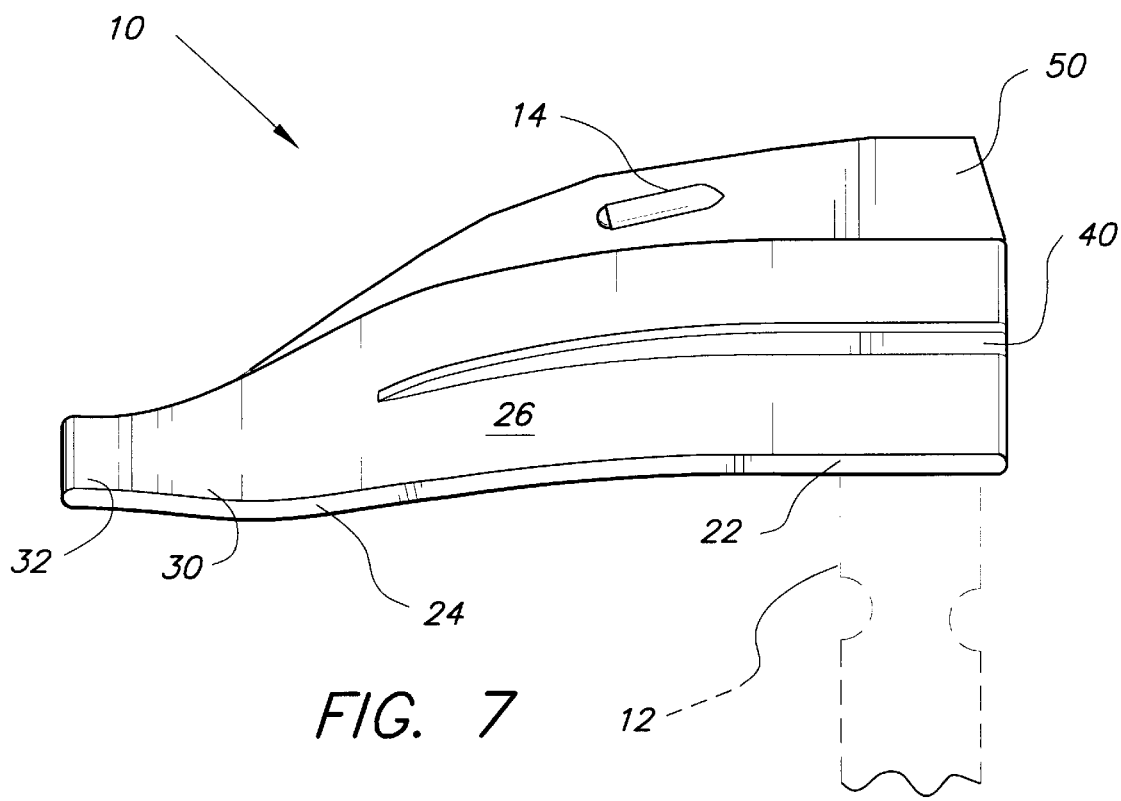
FIG. 7 is a top perspective view of an embodiment of the invention with a vertical wall and a raised area defining grooves on the blade.

The blade 10 of the present invention is further improved by the addition of raised areas 40 defining grooves on the top surface 26 of the blade 10, as seen in FIGS. 6 and 7. One of the grooves defined by the medial raised area 40 shown in the Figures may be used for guiding a tube over the top surface 26 of the blade 10 for insertion into the trachea, while the other groove preserves a line of sight to visualize the larynx and glottis.

The blade may be further improved by the addition of a vertical wall 50 having its bottom edge attached to the edge of the proximal portion 22a of the arcuate body 20 as shown in FIGS. 6 and 7. The vertical wall 50 may serve as a convenient location for mounting of the means for illumination 14. When the vertical wall is thickened, it serves as a bite block to prevent the patient from damaging his teeth or preventing intubation by involuntarily biting the blade 10 or the tube. The additional raised area 40 shown adjacent to the vertical wall 50 in FIG. 6 might be used for insertion of a suction catheter to remove any liquids in the mouth or throat obstructing visualization of the larynx.

In operation, for an endotracheal intubation, the patient's position is adjusted to align the airway for intubation. Unlike the Macintosh and Miller blades, which are inserted in the right side of the patient's mouth, the blade 10 of the present invention is inserted medially towards the center of the mouth, by virtue of the width of the blade 10 approaching the width of the mouth.

In further contrast, the tip of the Macintosh blade is inserted in the vallecula between the epiglottis and the base of the tongue, while the curved tip of the Miller blade is inserted behind the posterior edge of the epiglottis. The blade 10 of the present invention may be used in either manner, depending on the anatomy of the patient and the preference of the physician. Once the tip 30 is inserted in the proper location, the epiglottis is raised to open the airway to permit the insertion of the tube. The proper positioning of the tube in the airway is verified by x-ray or other means.

It is to be understood that the present invention is not limited to the embodiments described above, but encompasses any and all embodiments within the scope of the following claims.

I claim:

1. An improved blade for a laryngoscope having a handle, comprising:

a) an arcuate body having a proximal portion including a proximal end and a distal portion including a distal end, the body being substantially flat, having a convex top surface and a concave bottom surface, said proximal portion being configured and dimensioned to the width of a patient's mouth in order to depress and control the tongue of a patient during insertion of an endotracheal tube, said distal portion tapering in width from the proximal portion to the distal end, the distal portion being configured and dimensioned to enter a throat of the patient in order to raise the epiglottis for insertion of the endotracheal tube, wherein a median axis extending longitudinally through the proximal portion of the bottom surface of said arcuate body and a median axis extending longitudinally through the distal portion of the bottom surface of said arcuate body intersect to define an angle between and inclusive of 5 and 25 degrees;

b) means for connection to the laryngoscope handle connected to the proximal end of said arcuate body;

c) a tip at the distal end of said arcuate body, the tip having a point of inflection and a short tip extension from said point, the extension being substantially concave upwards; and d) means for illuminating the distal end of said arcuate blade.

2. The improved blade for a laryngoscope according to claim 1, wherein the top surface and the bottom surface of said arcuate body have a proximal portion having a width greater than 2 cm, the proximal portion having a substantially oblong shape, and a distal portion which tapers in width from the proximal portion to a width of not greater than 2 cm at the distal end of said arcuate body.

3. The improved blade for a laryngoscope according to claim 1, wherein the top surface and the bottom surface of said arcuate body have a proximal portion having a width of between 2 cm and 6 cm, the proximal portion having a substantially oblong shape, and a distal portion which tapers in width from the proximal portion to a width not greater than 2 cm at the distal end of said arcuate body, wherein the proximal portion of said arcuate body is configured and dimensioned to the width of a patient's mouth and the distal portion is configured and dimensioned to enter the patient's throat.

4. The improved blade for a laryngoscope according to claim 1, further comprising at least one raised area on the convex top surface of said arcuate body defining a plurality of grooves whereby the larynx may be visualized and whereby an endotracheal tube or suction catheter may be passed over the blade and inserted into the trachea.

5. The improved blade for a laryngoscope according to claim 4, further comprising a vertical wall having its bottom edge attached to an edge of the proximal portion of said arcuate body.

6. The improved blade for a laryngoscope according to claim 5, wherein said vertical wall is dimensioned and configured in thickness to serve as a bite block whereby the patient is prevented from damaging his teeth by biting said blade and from preventing intubation by biting the tube.

7. The improved blade for a laryngoscope according to claim 1, wherein said means for connection to the laryngoscope handle is attached to the bottom surface of said arcuate body and pivotally mounts the blade to the laryngoscope handle so that the blade is substantially parallel to the handle when not in use and substantially perpendicular to the handle to form an L-shape in use.

* * * * *